United States Patent [19]

Tilkens

[11] Patent Number: 5,189,265
[45] Date of Patent: Feb. 23, 1993

[54] CAP WITH HEARING ENHANCING STRUCTURE

[76] Inventor: Mark P. Tilkens, 1068 Westport Dr., Apartment 216, Port Washington, Wis. 53074

[21] Appl. No.: 669,844
[22] Filed: Mar. 15, 1991
[51] Int. Cl.⁵ .......................................... H04R 25/00
[52] U.S. Cl. .................................... 181/133; 181/136
[58] Field of Search ...................... 181/129, 133, 136; 2/10, 195, 197, 410, 423

[56] References Cited

U.S. PATENT DOCUMENTS

| | | | |
|---|---|---|---|
| D. 292,916 | 11/1987 | Ikeda | 181/136 |
| 1,364,662 | 1/1921 | Wagner | 2/410 |
| 3,497,874 | 3/1970 | Molitoris | 2/423 |
| 3,513,937 | 5/1970 | Robinson et al. | 181/129 |
| 3,618,698 | 11/1971 | McCabe et al. | 181/129 |
| 4,421,199 | 12/1983 | Vrana | 181/136 |
| 4,574,912 | 3/1986 | Fuss et al. | 181/129 |
| 4,768,613 | 9/1988 | Brown | 181/136 |
| 4,771,859 | 9/1988 | Breland | 181/136 |
| 4,872,218 | 10/1989 | Holt | 2/197 X |

*Primary Examiner*—Richard A. Wintercorn
*Assistant Examiner*—Khanh Dang
*Attorney, Agent, or Firm*—Andrus, Sceales, Starke & Sawall

[57] ABSTRACT

A hearing-enhancing device includes a cap adapted to be worn on a person's head, and a pair of hearing-enhancing members connectable to the cap. The cap size can be adjusted to accommodate varying user head sizes. The hearing-enhancing members each act to substantially enclose the person's ears leaving a forwardly facing opening allowing sound to enter therein, and are constructed so as to direct sound to the person's ears. A connection arrangement is provided between the cap and the hearing-enhancing members for allowing the members to be moved to varying locations on the cap, to provide proper positioning of the members even when the cap is adjusted to accommodate different user head sizes.

6 Claims, 2 Drawing Sheets

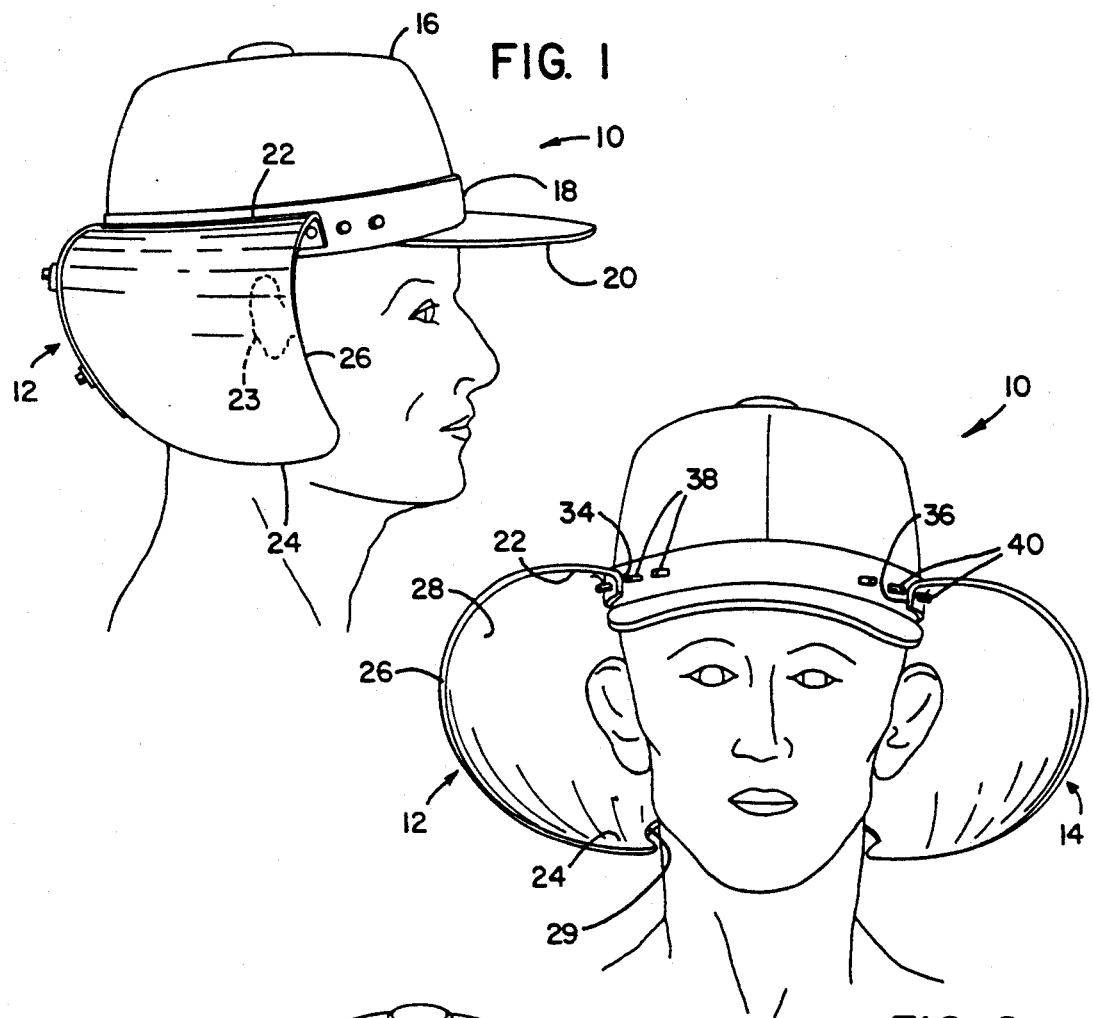
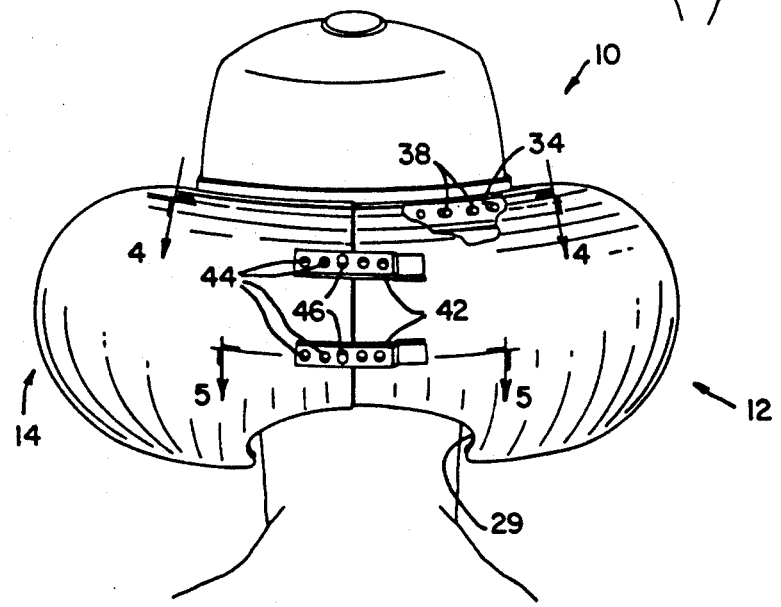

CAP WITH HEARING ENHANCING STRUCTURE

BACKGROUND OF THE INVENTION

This invention relates generally to a device for enhancing a person's hearing, and more particularly to such a device which is worn on the person's head.

Devices are known which are adapted to be worn on a person's head and which includes structure for directing sound toward the person's ears. Such devices are shown, for example, in Brown U.S. Pat. No. 4,768,613 and Breland U.S. Pat. No. 4,771,859. The Brown patent shows a head band or cap arrangement, in which a pair of sound-reflecting plates are positioned on opposite sides of the device behind the person's ears. The Breland patent discloses shell-type structures adapted for placement over the person's ears and interconnected with an over-the-head band.

The present invention has as its object to provide a cap having improved structure for directing sound toward a person's ears. Another object of the invention is to provide a cap which can be varied in size to accommodate varying head sizes, and with which the position of the hearing-enhancing structure can be adjusted to accommodate varying head sizes and varying ear positions.

In accordance with one aspect of the invention, a hearing-enhancing device comprises a cap which includes a band for encircling a person's head, with the band being adjustable to varying sizes. The device further includes a pair of hearing-enhancing members located on opposite sides of the cap and connected to the band. Each member is provided with a curved interior surface which cooperates with a side of the person's head to define a conch-shaped internal cavity within which the person's ear is located. Each hearing-enhancing member has a leading edge which is adapted to be located forwardly of the person's ear when the cap is worn on a person's head. A variable position connection arrangement is provided between each hearing-enhancing member and the band, for allowing the position of each member to be adjusted on the band. In this manner, the leading edge of each hearing-enhancing member can be positioned forwardly of the person's ear when the band is adjusted from one size to another.

The band of the cap may be adjustable to varying sizes by means of a conventional peg-and-opening system, in which one or more pegs provided at one end of the band can be engaged within one or more of a series of openings formed in the other end of the band.

The connecting arrangement between each hearing-enhancing member and the band can also take the form of a peg-and-opening system, in which a series of spaced pegs are provided along the band. The upper portion of the hearing-enhancing member includes a lip having spaced openings for engagement with selected pegs, to allow the member to be moved to varying discrete locations on the band.

Each hearing-enhancing member includes a rear surface which is adapted to wrap around the rear of the person's head, with the rear surfaces of the hearing-enhancing members overlapping each other. A connecting arrangement is provided for securing the rear surfaces of the members together, with the connecting arrangement accommodating movement of the hearing-enhancing members to varying positions on the band.

In accordance with another aspect of the invention, a hearing-enhancing device comprises a cap adapted to be worn on a person's head and including a band, and a pair of hearing-enhancing members located on opposite sides of the cap and connected to the band. Each hearing-enhancing member is located over one of the person's ears and has an upper surface located above and forwardly of the ear, a lower surface located below and forwardly of the ear, and a leading edge extending between the upper and lower surfaces and located forwardly of the ear. Each member has a curved interior surface, which is arcuate in cross-section, which interconnects the upper and lower surfaces and extends rearwardly from the leading edge, wherein the forward portion of the interior surface is spaced outwardly from the side of the person's head and a rearward portion of the interior surface is located closely adjacent the rear portion of the person's head. The curved interior surface cooperates with the person's head to define a conch-shaped internal cavity within which the ear is located.

The structure of the hearing-enhancing members as summarized above is employed in connection with an adjustable size band, with an adjustable connection arrangement being interposed between the band and each hearing-enhancing member for ensuring proper positioning of the hearing-enhancing member when the cap is adjusted to varying sizes.

Various other features, objects and advantages of the invention will be made apparent upon consideration of the following description taken together with the drawings.

BRIEF DESCRIPTION OF THE DRAWINGS

The drawings illustrate the best mode presently contemplated of carrying out the invention.

In the drawings:

FIG. 1 is a side elevation view of a person wearing the hearing-enhancing device of the invention;

FIG. 2 is a front elevation view of a person wearing the hearing-enhancing device of the invention;

FIG. 3 is a rear elevation view of a person wearing the hearing-enhancing device of the invention;

DETAILED DESCRIPTION OF THE PREFERRED EMBODIMENT

Figure 4:
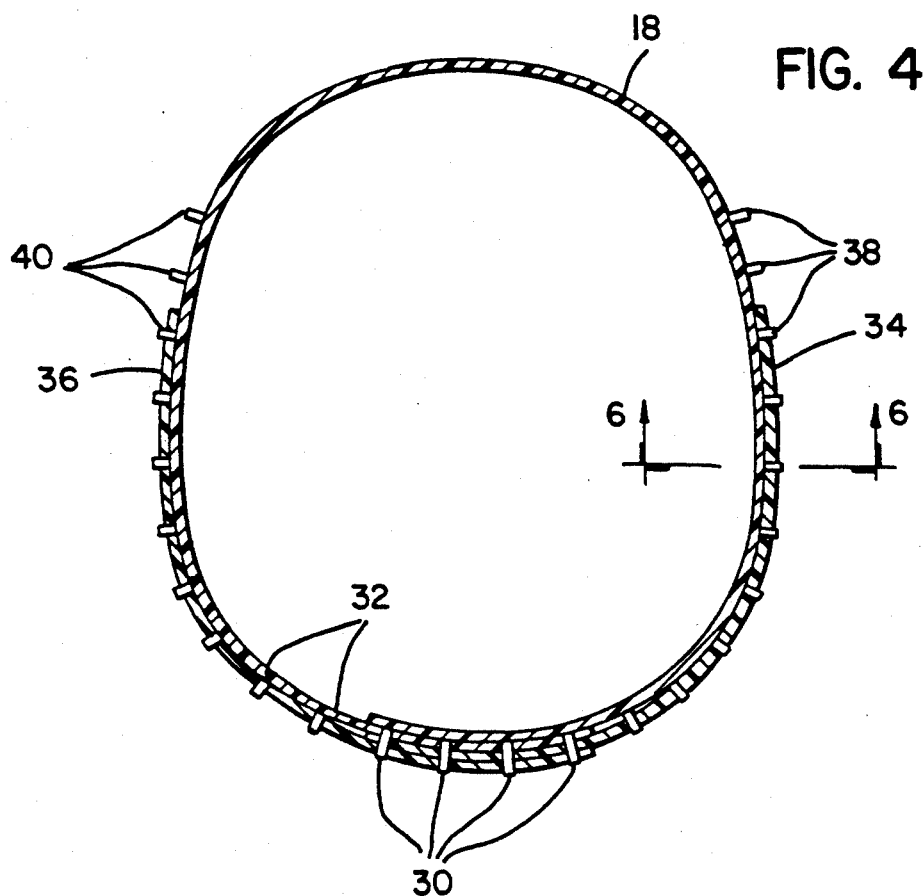
FIG. 4 is a section view taken generally along line 4—4 of FIG. 3.

FIGS. 1, 2 and 3 illustrate a hearing-enhancing device consisting of a cap 10 to which a pair of hearing-enhancing members 12, 14 are connected. The device is shown worn on a person's head.

Cap 10 generally comprises an upper portion 16 for enclosing the top of the person's head, with a band 18 being secured at the lower edge of upper portion 16. A visor portion 20 extends forwardly from band 18 to shade the person's eyes, as is known.

While band 18 is illustrated as being external, it is to be appreciated that an internal band could satisfactorily be employed on cap 10, as could a combination internal/external band structure.

Hearing-enhancing members 12, 14 are essentially mirror images of each other. Member 12 will be described in detail, with the understanding that such description applies with equal force to member 14.

Hearing-enhancing members 12 are 14 are preferably constructed of a lightweight molded plastic material, such as ABS, which is formed to a shape as shown in the drawing figures and as will be described.

Referring to FIGS. 1–3, member 12 includes an upper surface 22 located above the person's ear, shown at 23, and a lower surface 24 located below the person's ear. Upper and lower surfaces 22, 24 extend in a front-to-rear direction, terminating at their forward end forwardly of the person's ear 23. A leading edge 26 of member 12 extends between upper and lower surfaces 22, 24, respectively, and is also disposed forwardly of the person's ear 23.

An inner wall 28 extends rearwardly from leading edge 26 between upper and lower surfaces 22, 24. Wall 28 provides a curved interior surface facing the side of the person's head, and is substantially arcuate in cross section. Referring to FIG. 2, wall 28 at leading edge 26 is C-shaped in elevation, with the magnitude of the arc defined by its cross section decreasing toward the rear of the person's head. Wall 28 is spaced outwardly from the side of the person's head at leading edge 26, and is located closely adjacent the rear of the person's head at its rearward end. In this manner, the curved interior surface of wall 28 cooperates with the side and rear of the person's head to define a cup shape having an internal cavity resembling that of a conch, within which the person's ear 23 is located.

Lower surface 24 defines an arcuate edge which cooperates with an arcuate edge 29 defined by the lower surface of hearing-enhancing member 14 to define an opening which receives the neck of the person therewith.

The material from which hearing-enhancing members 12, 14 is constructed provides a smooth acoustically reflective interior surface which directs sounds from in front of the person toward the person's ears, while shielding sounds coming from behind and from the sides of the person. This structure has been found particularly useful in hunting of game such as deer, to enhance a person's ability to hear noises which otherwise may be drowned out by background noise.

Referring to FIG. 4, band 18 of cap 10 can be adjusted to varying sizes. As shown in FIG. 4, the ends of band 18 overlap each other at the rear of cap 10, and a peg-and-opening arrangement is provided for adjusting the size of band 18. A series of spaced long pegs 30 are provided at one end of band 18, and the other end of band 18 is provided with a series of openings 32 having spacing equal to that of pegs 30. Pegs 30 are engageable within selected ones of openings 32 for adjusting band 18 to differing sizes.

Referring again to FIGS. 1 and 3, an upper lip 34 depends from upper surface 22 of hearing-enhancing member 12. Similarly, a lip 36 depends from the upper surface of hearing-enhancing member 14. Lips 34, 36 are arcuate in plan, and are provided with a series of spaced openings along their length.

One side of band 18 is provided with a series of equally spaced outwardly projecting short pegs 38 extending forwardly from long rear pegs 30. The other side of band 18 is similarly provided with a series of equally spaced outwardly projecting short pegs 40 extending forwardly from long rear pegs 30. The spacing of pegs 38 is identical to that of the openings in lip 34 of hearing-enhancing member 12, while the spacing of pegs 40 is identical to that of the openings in lip 36 of hearing-enhancing member 14.

Short pegs 38, 40 extend forwardly from long rear pegs 30, and terminate rearwardly of the front portion of band 18.

Pegs 38, 40 and the openings in lips 34, 36 allow hearing-enhancing members 12, 14 to be moved to varying discrete positions along the length of band 18. As noted previously, it is most advantageous for the leading edges, such as 26, of hearing-enhancing members 12, 14 to be located forwardly of the person's ears so as to ensure that unwanted sounds from the person's sides are shielded. Accordingly, the person can detach hearing-enhancing members 12, 14 and position them on pegs 38, 40 to ensure that the leading edges, such as 26, of hearing-enhancing members 12, 14 are located forwardly of the person's ears.

When cap 10 is to be worn on a person having a different sized head, hearing-enhancing members 12, 14 are first detached an long pegs 30 engaged with appropriate openings 32 to attain the desired size of band 18. Hearing-enhancing members 12, 14 are then reattached by engaging the opening in lips 34, 36 with short pegs 38, 40 in a position such that the leading edges of members 12, 14 are located forwardly of the person's ears.

Figure 5:
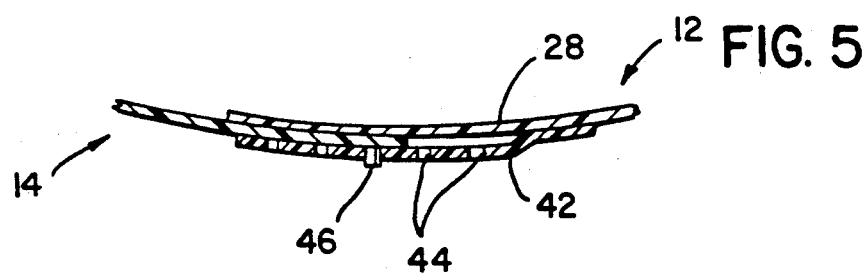
FIG. 5 is a partial sectional view taken generally along line 5—5 of FIG. 3.
Figure 6:
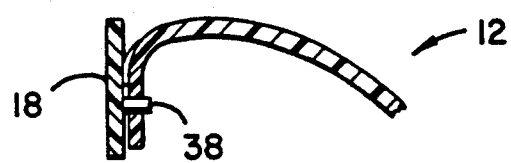
FIG. 6 is a partial sectional view taken generally along line 6—6 of FIG. 4.

Referring to FIG. 4, the rearwardmost portions of lips 34 and 36 are provided with openings through which long pegs 30 extend, to fix the position of the rear portion of members 12, 14 on band 18. The rearwardmost extent of the walls, such as 28, forming members 12, 14 overlap each other. As shown in FIGS. 3 and 5, a pair of straps 42 are connected at the rearwardmost portion of wall 28 of member 12, and each strap 42 is provided with a series of spaced openings 44. The rearwardmost portion of the wall of member 14 is provided with a pair of pegs 46 adjacent its rear end. Pegs 46 are engageable with a selected one of openings 44 to interconnect the rearward portions of hearing-enhancing members 12, 14. This structure accommodates movement of members 12, 14 to varying positions on band 18 and allows the overlapping rear portions of members 12, 14 to be secured together. With this arrangement, a narrow channel is defined between the rear portion of the person's head and the inner wall of the rear portion of members 12, 14.

The structure as shown and described provides a hearing-enhancing device which is simple in construction and manufacture, and which necessitates manufacture of only one size, which can be varied to accommodate different user head sizes. In addition, the structure providing variable positioning of the hearing-enhancing members allows a user to adjust the location of the members to provide optimum hearing in a desired setting. Further, the structure allows the device, once purchased, to be used by a number of users if desired.

Various alternatives and embodiments are contemplated as being within the scope of the following claims particularly pointing out and distinctly claiming the subject matter regarded as the invention.

I claim:

1. A hearing enhancing device adapted to be worn on a person's head, comprising:
   a cap including a band for encircling the person's head, the band being adjustable to varying sizes to accommodate varying head sizes;
   a pair of hearing-enhancing members located on opposite sides of the cap and connected to the band, each member having a curved interior surface which cooperates with a side of the person's head to define an internal cavity within which one of the person's ears is located when the cap is placed on the person's head, wherein each hearing enhancing member includes a leading edge adapted to be located forwardly of one of the person's ears; and a variable position connection arrangement interposed between each hearing-enhancing member and the band, for providing adjustment of each member on the band to enable the leading edge of each hearing-enhancing member to be positioned forwardly of one of the person's ears when the band is adjusted from one size to another, wherein the variable position connection arrangement comprises a series of openings provided in each hearing-enhancing member and a series of pegs provided on the band, the pegs being engageable within the openings for accommodating movement of each member to varying discrete locations on the band.

2. A hearing enhancing device adapted to be worn on a person's head, comprising:
   a cap including a band for encircling the person's head, the band being adjustable to varying sizes to accommodate varying head sizes;
   a pair of hearing-enhancing members located on opposite sides of the cap and connected to the band, each member having a curved interior surface which cooperates with a side of the person's head to define an internal cavity within which one of the person's ears is located when the cap is placed on the person's head, wherein each hearing-enhancing member includes a leading edge adapted to be located forwardly of one of the person's ears; and
   a variable position connection arrangement interposed between each hearing-enhancing member and the band, for providing adjustment of each member on the band to enable the leading edge of each hearing-enhancing member to be positioned forwardly of one of the person's ears when the band is adjusted from one size to another;
   wherein each member includes a rear surface adapted to wrap around behind the person's head, wherein the rear surfaces of the hearing-enhancing members overlap each other, and further comprising a connection arrangement for securing the rear surfaces of the hearing-enhancing members together, the connection arrangement accommodating movement of the hearing-enhancing members to varying positions on the band.

3. The device of claim 2, wherein the connection arrangement comprises one or more pegs provided on one of the members and a strap having a series of openings connected to the other of the members, wherein one or more of the openings are engageable with one or more of the pegs.

4. A hearing-enhancing device adapted to be worn on a person's head, comprising:
   a cap including a band for encircling the person's head, the band including an arrangement for adjusting the band to varying sizes to allow the cap to be worn on persons having heads of different sizes;
   a pair of hearing-enhancing members located on opposite sides of the cap and connected to the band, each member being located over one of the person's ears and having an upper surface located above and forwardly of the person's ear, a lower surface located below and forwardly of the person's ear, a leading edge extending between the upper and lower surfaces and located forwardly of the person's ear, and a curved interior surface, arcuate in cross-section, interconnecting the upper surface and the lower surface and extending rearwardly from the leading edge, wherein a forward portion of the interior surface is spaced outwardly from the side of the person's head and a rearward portion of the interior surface is located closely adjacent the rear portion of the person's head, wherein the curved interior surface cooperates with the person's head to define a conch-shaped internal cavity within which the ear is located; and
   an adjustable connection arrangement interposed between the band and each hearing-enhancing member for allowing positioning of each member to varying locations on the band to position the upper surface, lower surface and leading edge of each member forwardly of the ear when the band is adjusted from one size to another, wherein the adjustable connection arrangement between the band and each hearing-enhancing member comprises a series of openings provided in each hearing-enhancing member and a series of pegs provided on the band, the pegs being engageable within the openings for accommodating movement of each member to varying discrete locations on the band.

5. A hearing-enhancing device adapted to be worn on a person's head, comprising:
   a cap including a band for encircling the person's head, the band including an arrangement for adjusting the band to varying sizes to allow the cap to be worn on persons having heads of different sizes;
   a pair of hearing-enhancing members located on opposite sides of the cap and connected to the band, each member being located over one of the person's ears and having an upper surface located above and forwardly of the person's ear, a lower surface located below and forwardly of the person's ear, a leading edge extending between the upper and lower surfaces and located forwardly of the person's ear, and a curved interior surface, arcuate in cross-section, interconnecting the upper surface and the lower surface and extending rearwardly from the leading edge, wherein a forward portion of the interior surface is spaced outwardly from the side of the person's head and a rearward portion of the interior surface is located closely adjacent the rear portion of the person's head, wherein the curved interior surface cooperates with the person's head to define a conch-shaped internal cavity within which the ear is located;
   wherein each hearing-enhancing member includes a rear surface adapted to wrap around behind the person's head, wherein the rear surfaces of the hearing-enhancing members overlap each other, and further comprising a connecting arrangement for securing the rear surfaces or the members together, the connecting arrangement accommodating movement of the hearing-enhancing members to varying positions on the band.

6. A hearing enhancing device adapted to be worn on a person's head, comprising:
   a cap including a band for encircling the person's head; and
   a pair of hearing-enhancing members located on opposite sides of the cap and connected to the band, each member being located over one of the person's ears and having an upper surface located above and forwardly of the person's ear, a lower surface located below and forwardly of the person's ear, a leading edge extending between the upper and lower surfaces and located forwardly of the person's ear, and a curved interior surface, arcuate in cross-section, interconnecting the upper surface and the lower surface and extending rearwardly from the leading edge, wherein a forward portion of the interior surface is spaced outwardly from the side of the person's head and a rearward portion of the interior surface is located closely adjacent the rear portion of the person's head, wherein the curved interior surface cooperates with the person's head to define a conch-shaped internal cavity within which the ear is located, and wherein the lower surfaces of each hearing-enhancing member cooperate to define an arcuate opening adapted to receive the person's neck therewithin.

* * * * *